United States Patent [19]
Slater

[11] Patent Number: 5,395,386
[45] Date of Patent: Mar. 7, 1995

[54] ENDOSCOPIC PERICARDIAL SCISSORS

[75] Inventor: Charles R. Slater, Fort Lauderdale, Fla.

[73] Assignee: Symbiosis Corporation, Miami, Fla.

[21] Appl. No.: 114,909

[22] Filed: Aug. 31, 1993

Related U.S. Application Data

[63] Continuation-in-part of Ser. No. 837,046, Feb. 18, 1992, which is a continuation of Ser. No. 521,766, May 10, 1990, Pat. No. 5,133,727, and Ser. No. 922,023, Jul. 28, 1992, Pat. No. 5,331,971, which is a continuation of Ser. No. 680,392, Apr. 4, 1991, Pat. No. 5,192,298, and Ser. No. 944,202, Sep. 11, 1992, Pat. No. 5,241,968, which is a continuation-in-part of Ser. No. 780,013, Oct. 21, 1991, Pat. No. 5,203,785.

[51] Int. Cl.⁶ .............................................. A61B 17/32
[52] U.S. Cl. .................................. 606/170; 606/174; 606/205; 128/751
[58] Field of Search .......................... 128/749, 751; 606/205–208, 167, 170

[56] References Cited

U.S. PATENT DOCUMENTS

| | | |
|---|---|---|
| 2,618,268 | 11/1952 | English . |
| 2,668,537 | 2/1954 | Kapp . |
| 4,024,869 | 5/1977 | Bonnet . |
| 4,258,716 | 3/1981 | Sutherland . |
| 4,522,206 | 6/1985 | Whipple et al. . |
| 4,763,669 | 8/1988 | Jaeger ................... 128/751 |
| 4,880,015 | 11/1989 | Nierman ................. 128/751 |
| 4,985,030 | 1/1991 | Melzer et al. ........... 606/51 |
| 5,147,373 | 9/1992 | Ferzli .................... 606/144 |
| 5,217,460 | 6/1993 | Knoepfler ............... 606/52 |
| 5,275,608 | 1/1994 | Forman et al. ......... 606/205 X |
| 5,282,826 | 2/1994 | Quadri .................. 606/207 |

*Primary Examiner*—Lee S. Cohen
*Assistant Examiner*—Samuel G. Gilbert
*Attorney, Agent, or Firm*—David P. Gordon

[57] ABSTRACT

A pericardial endoscopic scissors is provided and generally comprises a hollow tube with a clevis coupled thereto, first and second scissor blades laterally offset from each other and both having elongate straight blade edges angled at about 45 degrees relative to the hollow tube, with the first scissor blade pivotally engaging the clevis so that its blade can angle about 90 degrees relative to the hollow tube in an open position, a rod extending through the hollow tube and coupled to the pivoting first scissor blade, and an actuator engaging the rod and imparting reciprocal motion thereto, which reciprocal motion is translated to pivotal motion of the first scissor blade. The fixed second scissor blade is provided at its distal end with an integral probe element which is laterally offset relative to and indented from the straight blade edge. The probe element extends away from the second scissor blade toward the first scissor blade, and the second scissor blade together with the probe element provide a rounded presenting surface. Likewise, the distal end of the first scissor blade presents a rounded surface substantially adjacent the rounded presenting surface of said second blade member. The probe element of the second scissor blade does not contact the first scissor blade during a scissor cutting action.

20 Claims, 6 Drawing Sheets

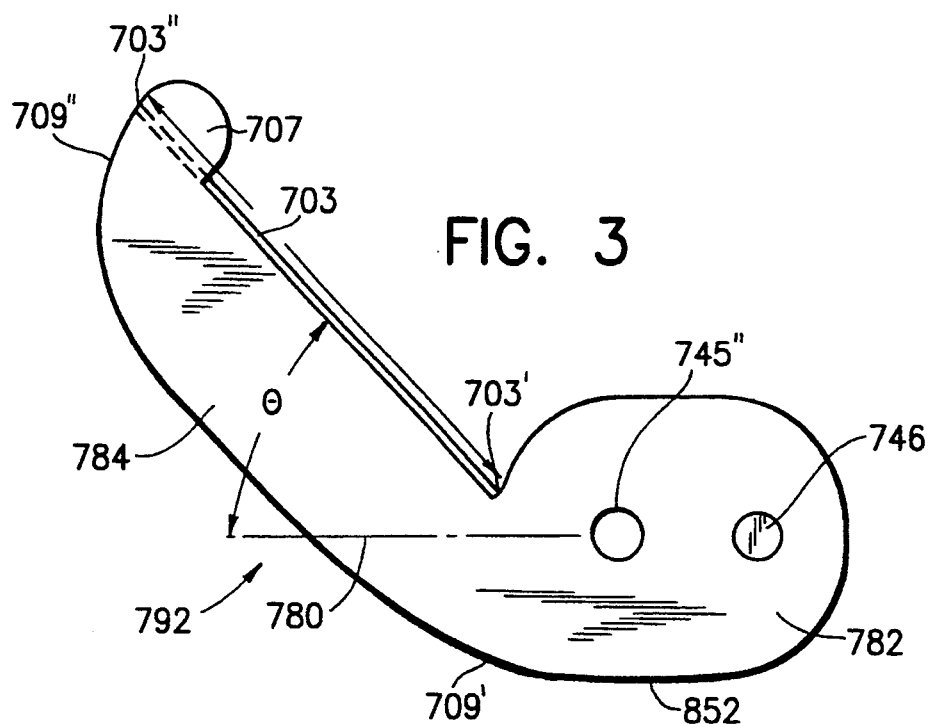
FIG. 3
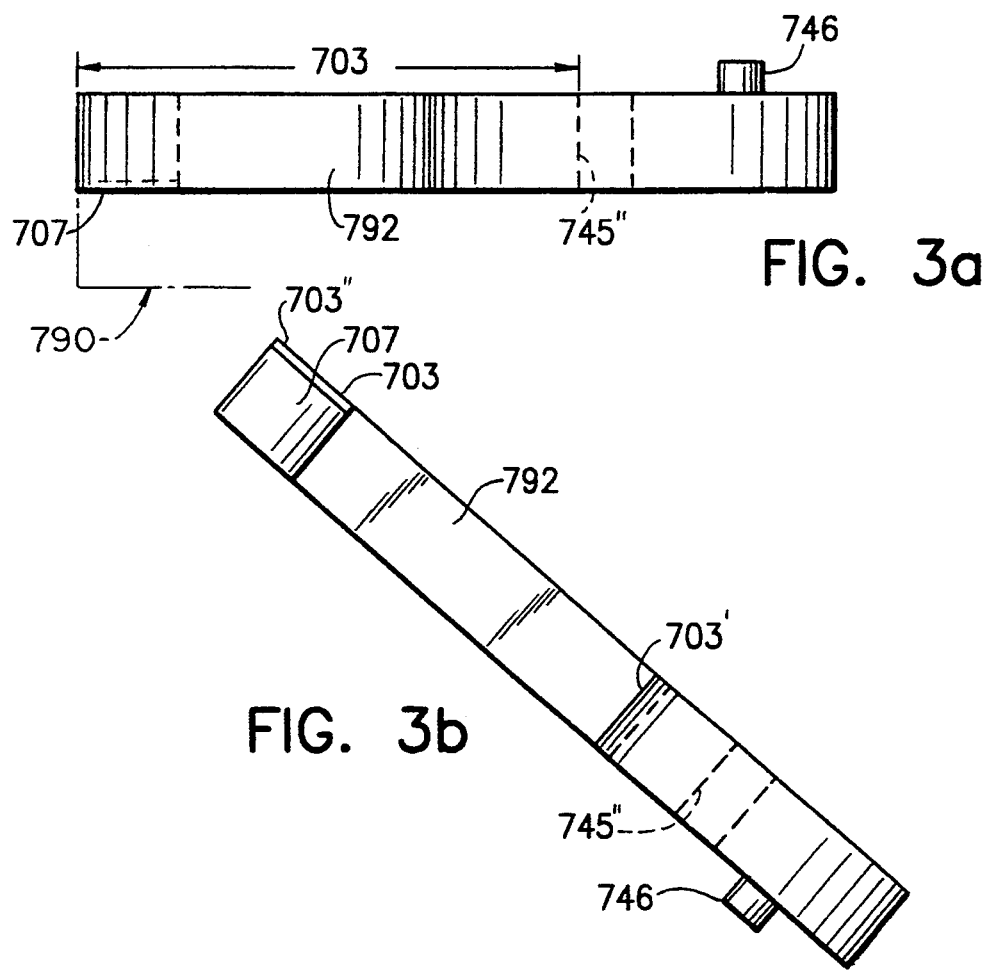
FIG. 3a
FIG. 3b

CLOSED POSITION

OPEN POSITION

ENDOSCOPIC PERICARDIAL SCISSORS

This is a continuation-in-part of pending Ser. No. 07/837,046, filed Feb. 28, 1992, which is a continuation of Ser. No. 07/521,766, filed May 10, 1990, now issued as U.S. Pat. No. 5,133,727, and of Ser. No. 07/922,023, filed Jul. 28, 1992, which is a continuation of Ser. No. 07/680,392, filed Apr. 4, 1991, now issued as U.S. Pat. No. 5,192,298, and of Ser. No. 07/944,202, filed Sep. 11, 1992, now U.S. Pat. No. 5,241,968, which is a continuation-in-part of Ser. No. 07/780,013, filed Oct. 21, 1991, now issued as U.S. Pat. No. 5,203,785, which are all hereby incorporated by reference herein in their entireties.

BACKGROUND OF THE INVENTION

The present invention broadly relates to surgical instruments. More particularly, the invention relates to endoscopic surgical instruments having end effectors in the form of blunt ended scissors. Such blunt ended scissors are useful in procedures which involve the cutting by scissoring action of a first structure or tissue which is adjacent another structure or tissue to which damage must be avoided.

The endoscopy and laparoscopy procedures have recently become widely practiced surgical procedures. The endoscopy and laparoscopy procedures typically involve incising through body walls (e.g., the abdominal wall) for examining, viewing and/or operating on the ovaries, uterus, gall bladder, bowels, appendix, etc. Typically, trocars are utilized for creating the incisions. Trocar tubes are left in place so that the endoscopic or laparoscopic surgical tools may be inserted through the tube. A camera, magnifying lens, or other optical instrument is often inserted through one trocar tube, which for the laparoscopy procedure is generally located at the navel incision, while a cutter, dissector, extractor, or other surgical instrument is inserted through another trocar tube for purposes of manipulating and/or cutting the internal organ. Sometimes it is desirable to have several trocar tubes in place at once in order to receive several surgical instruments. In this manner, organ or tissue may be grasped with one surgical instrument, and simultaneously may be cut or stitched with another surgical instrument; all under view of the surgeon via the optical instrument.

Previous to the present invention, different endoscopic and laparoscopic tools have utilized scissor end effectors of several types; e.g., curved, hooked, and straight. While generally effective for cutting, the endoscopic/laparoscopic scissors of the art have the drawback that they are relatively sharp at their distal ends, and when used for cutting tissue or a structure (e.g., the pericardial wall) which is adjacent an organ or another structure (e.g., the heart) which is sensitive to irritation, the sharp distal ends of the prior art scissors can cause trauma to the adjacent organ when opening and closing to effect the cutting action.

SUMMARY OF THE INVENTION

It is therefore an object of the invention to provide blunt ended scissors end effectors for endoscopic and laparoscopic instruments.

It is another object of the invention to provide small diameter pericardial scissors intended for insertion through a trocar tube where the cutting line is angled relative to the longitudinal axis of the trocar tube, and where the presenting face of the scissors when moved along the longitudinal axis of the trocar tube is blunt.

It is a further object of the invention to provide an endoscopic/laparoscopic pericardial scissors where rotation of one blade to effect cutting action does not result in movement of the proximal end of that blade beyond the periphery of the proximal end of the non-rotating blade.

In accord with the object of the invention, a pericardial endoscopic scissors is provided and generally comprises a hollow tube with a clevis coupled thereto, first and second scissor blades laterally offset from each other and both having elongate straight blade edges angled at about 45 degrees relative to the hollow tube, with the first scissor blade pivotally engaging the clevis so that its blade can angle about 90 degrees relative to the hollow tube in an open position, a rod extending through the hollow tube and coupled to the pivoting first scissor blade, and an actuator engaging the rod and imparting reciprocal motion thereto, which reciprocal motion is translated to pivotal motion of the first scissor blade. The fixed second scissor blade is provided at its distal end with an integral probe element which is laterally offset relative to and indented from the straight blade edge. The probe element extends away from the second scissor blade toward the first scissor blade, and the second scissor blade together with the probe element provide a rounded presenting surface. Likewise, the distal end of the first scissor blade presents a rounded surface substantially adjacent the rounded presenting surface of said second blade member. However, the probe element of the second scissor blade does not contact the first scissor blade during a scissor cutting action.

In accord with a preferred aspect of the invention, the first scissor blade is shaped at its proximal end such that when it rotates from an open position to a closed position and vice versa, the proximal end of the first scissor blade does not extend substantially below the bottom surface of the second scissor blade. In this manner, tissue or organs located below the scissors will not be irritated by the cutting action.

A better understanding of the pericardial scissors instrument of the invention, and additional advantages and objects of the invention will become apparent to those skilled in the art upon reference to the detailed description and accompanying drawings.

BRIEF DESCRIPTION OF THE DRAWINGS

FIG. 1A is a cross sectional view through FIG. 1 at an indicated location;

FIGS. 3, 3a and 3b show side elevation, top and bottom views of the fixed blade member of the device of FIG. 1;

DETAILED DESCRIPTION OF THE PREFERRED EMBODIMENT

Figure 1:
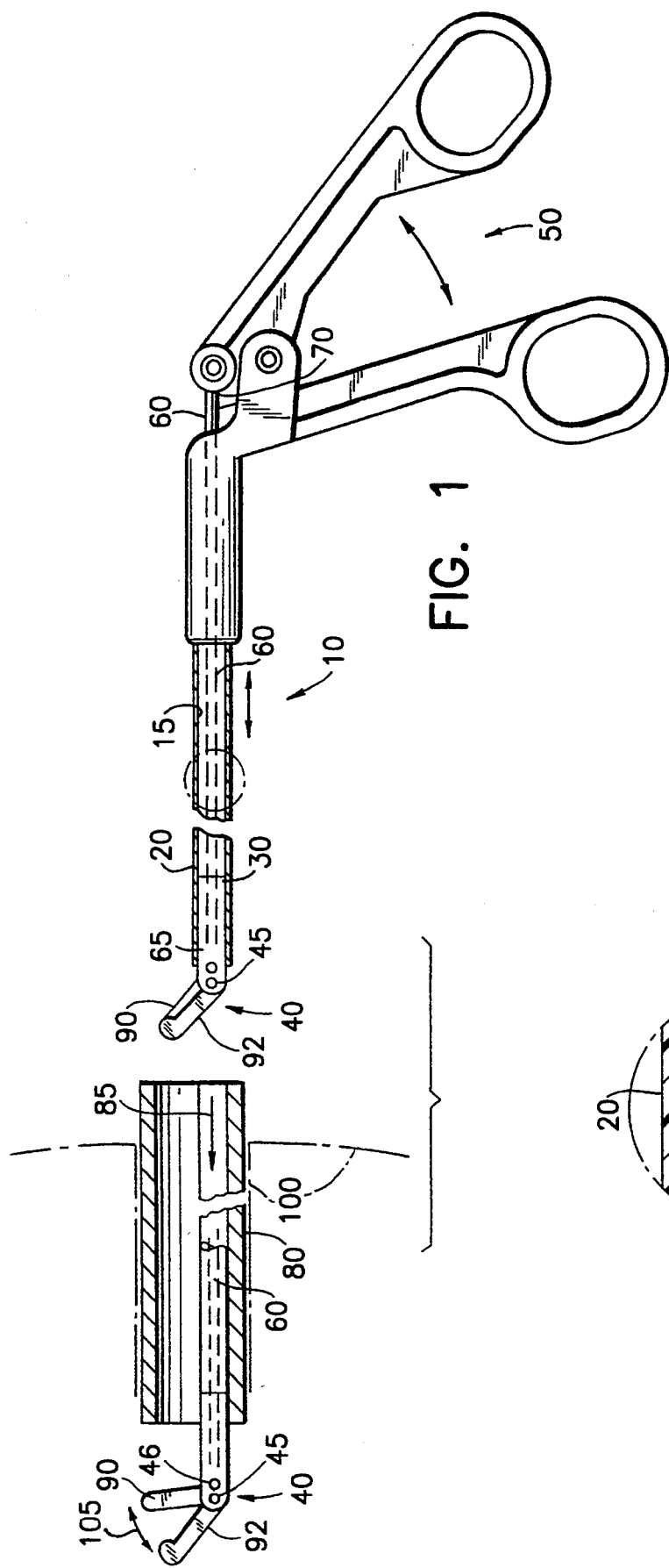
FIG. 1 is a side elevation view, partly in section, of the pericardial endoscopic instrument of the invention prior to insertion into a trocar tube, and, in partial phantom format, after insertion into a trocar tube.

With reference to FIGS. 1 and 1A, an endoscopic surgical instrument is indicated at 10. The endoscopic surgical instrument 10 preferably includes an aluminum tube 15 surrounded by a peripheral insulating shrink wrap layer of plastic 20, a clevis means 30, pericardial scissors end effectors 40, actuating means 50, and a push rod 60. The clevis means 30 is preferably a separately formed aluminum piece which fixedly engages aluminum tube 15. The clevis 30 also preferably engages the scissor elements 90, 92 of the pericardial scissors end effectors 40. As shown in FIG. 1, blade member 90 of the pericardial scissors is pivotally engaged to clevis 30 at pivot pin 45 and blade member 92 is fixedly engaged to the clevis 30 at pin 45 and post 46. The pericardial scissors end effectors 40 are preferably formed of a cobalt base alloy as disclosed in U.S. Patent co-owned U.S. Pat. No. 5,234,453 which is incorporated by reference herein, although it can be formed of other materials such as, e.g., stainless steel, if desired. The push rod 60, which is preferably formed of stainless steel, is engaged at its distal end 65 to the scissor element 90 as hereinafter more fully described, and is connected at 70, at its proximal end, to a manually operable actuating means 50. For purposes herein, the "distal end" of the instrument 10 or any part thereof, is the end closest to the surgical site and distant from the surgeon, while the "proximal end" of the instrument 10 or any part thereof, is the end most proximate the surgeon and distant the surgical site.

In use, the laparoscopy instrument 10 is inserted with the blades 90, 92 of the pericardial scissors in the closed position, into trocar tube 80, as indicated at the arrow 85 of FIG. 1. The distal portion of the instrument 10 passes through the trocar tube 80 into body incision 100. Upon the distal portion of the laparoscopy instrument 10 exiting the trocar tube 80, blade 90 can be opened and closed as indicated at 105 by reciprocal motion of push rod 60 which results from operation of the manual actuating means 50. As is discussed in more detail previously incorporated U.S. Pat. No. 5,192,298 the clevis effectively helps to translate the reciprocal motion of the push rod 60 into the end effector means action indicated at 105.

Additional detail regarding the endoscopic instrument 10 may be obtained by reference to previously incorporated U.S. Pat. No. 5,192,298. It is noted, however, that the preferred embodiment of the pericardial scissors of the invention is a single acting tool with one of the end effector blades stationary such as in parent application U.S. Ser. No. 07/744,202.

Figure 2:
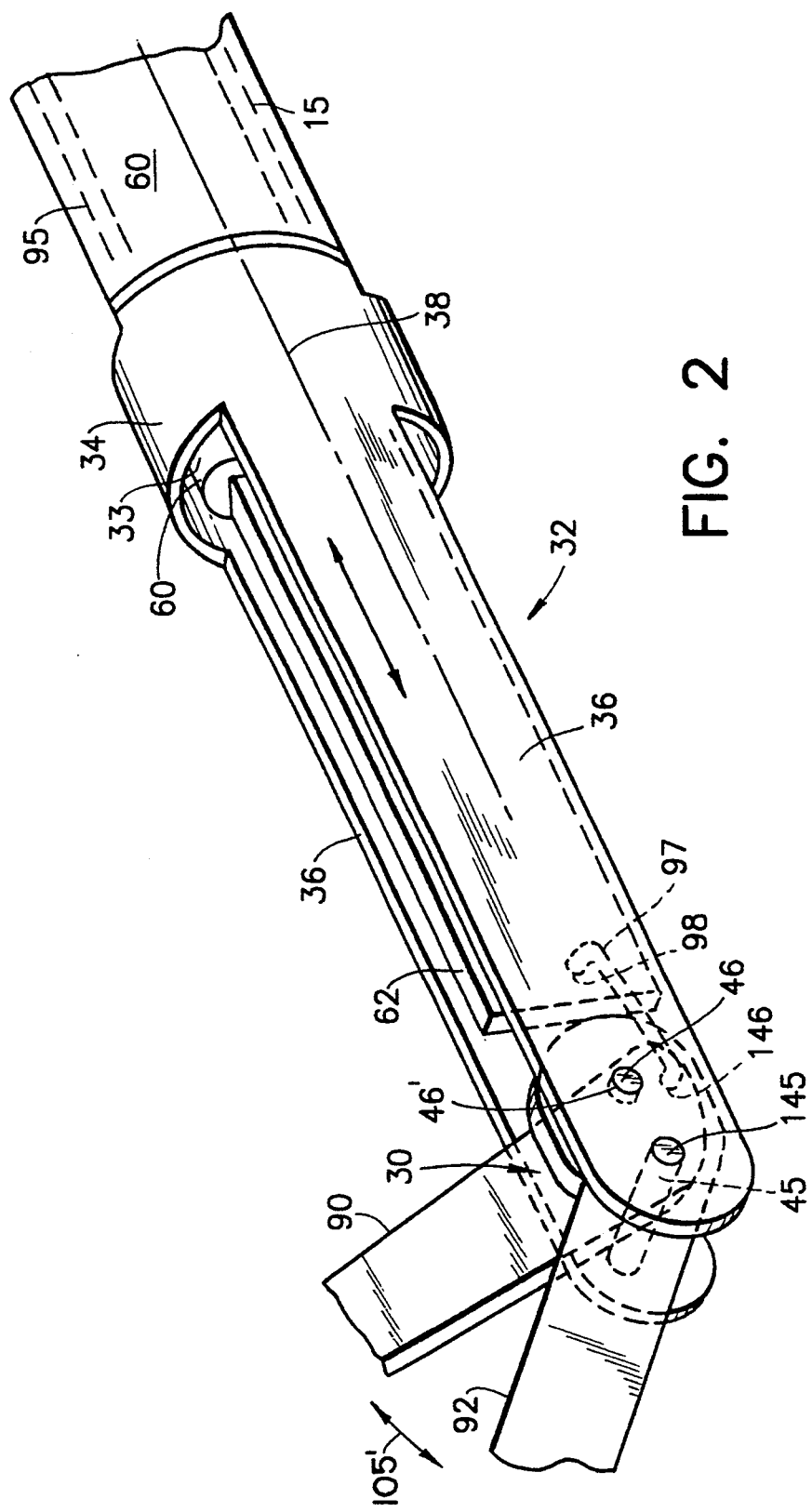
FIG. 2 is a perspective view of a clevis element usable in conjunction with the instrument of the invention.

Turning to FIG. 2, a preferred configuration of the clevis 30 for use with the atraumatic scissors of the present invention is seen. The clevis has a knurled proximal portion 95 for mating with the end of the aluminum tube 15, and a pivot-supporting generally U-shaped distal portion 32 for holding the end effector means 40 comprising members 90, 92. The proximal portion 34 of the clevis is preferably hollow, as indicated at 33, to permit the push rod 60, with its flattened terminal portion 62 to extend therethrough. The distal portion 32 of the clevis 30 is provided with a pivot pin 45 which is generally perpendicular, i.e. transverse, to the legs 36 of the clevis. In addition, where a single acting end effector is provided as in the preferred embodiment, one of the the legs of clevis 30 is provided with a hole 46'. The fixed end effector blade 92 of the single acting instrument is provided with a transverse or lateral protrusion 46 which extends into hole 46'. As a result, fixed blade 92 is fixed relative to the clevis 30 by engagement of protrusion 46 in hole 46' and by engagement of hole 145 at pivot pin 45. On the other hand, the pivoting blade member 90 is engaged at through hole 146 by a metal coupling member 97 to the flattened distal end 62 of push rod 60. Flattened distal end 62 is engaged to coupling member 97 at through hole 98. Upon actuation of push rod 60 as indicated by the arrows along the longitudinal axis of the rod 60, blade member 90 moves pivotally around pin 45 to provide the scissor action indicated at 105' while blade member 92 remains stationary. Double acting hook scissors are easily obtained by eliminating the protrusion 46 and hole 46' and by substituting an additional metal link or staple member as is disclosed in previously incorporated U.S. Pat. No. 5,192,298.

Figure 5A:
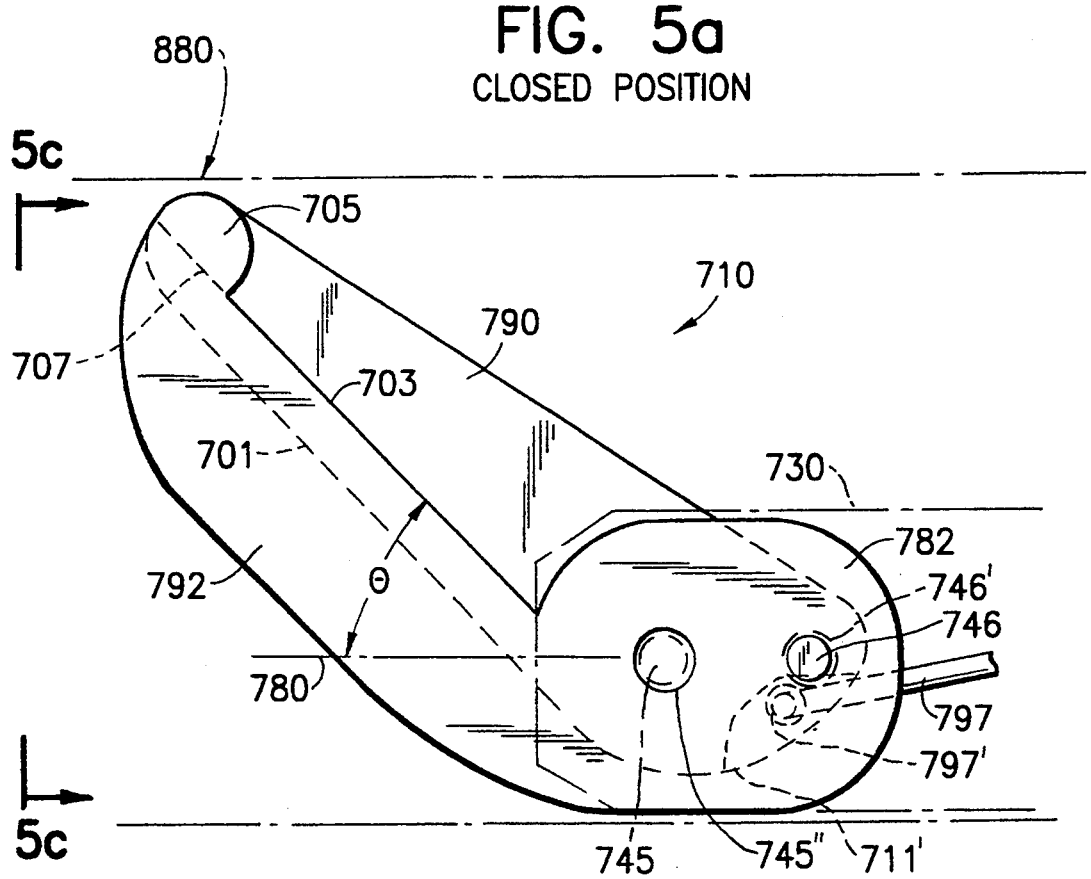
FIGS. 5a and 5b are side elevation views of the pericardial scissors of the present invention in a fully closed position and a fully open position respectively.
Figure 5C:
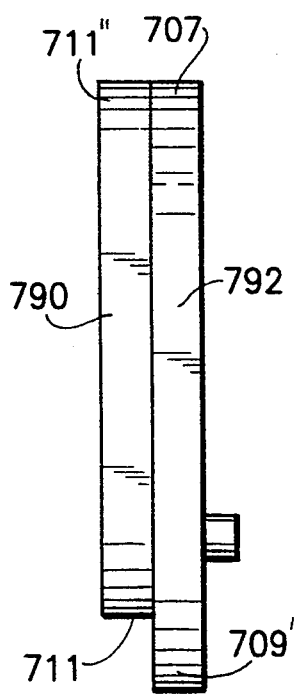
FIG. 5c is a front view of the scissors of FIG. 5a along line 5c—5c thereof.
Figure 5B:
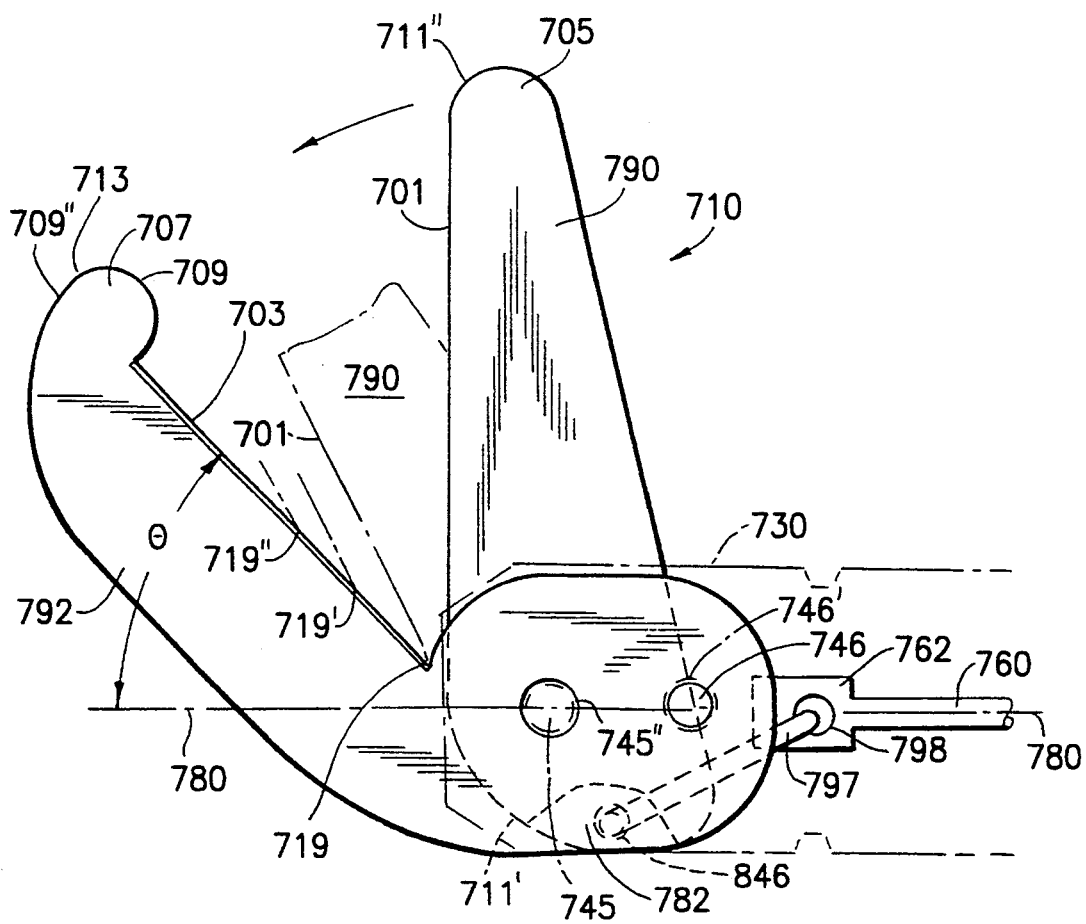

In accord with the invention, the stationary (fixed) blade member 792 of the pericardial scissors is seen in FIGS. 3, 3a, and 3b, where FIGS. 3a and 3b are respectively top and bottom views of FIG. 3. Blade member 792 includes has a proximal base portion 782 and a distal blade portion 784. The proximal base portion includes a boss 746 for mating with a hole (746') in a clevis (as seen in FIGS. 5a and 5b), and a hole 745" for mating with rod 745 of a clevis. With the two mating locations, as discussed above with reference to FIG. 2, blade member 792 is fixed relative to the clevis and will not rotate thereabout.

As seen in FIG. 3, the distal portion 784 of the fixed blade member 792 is angled at an angle Θ relative to a longitudinal axis 780 which itself is either parallel to or identical to the longitudinal axis of the tool. Distal portion 784 includes a slightly tapered straight blade 703 which extends from the proximal portion 782 of the blade member 792 (at 703') to its most distal end (703"). At the distal end, the fixed blade member includes an integral rounded, terminal probe element 707 which extends arcuately away from and substantially transverse to the blade 703. As seen in FIGS. 3a and 3b, the rounded probe element 707 is slightly offset from the blade edge 703. In this manner, and as discussed in great detail in parent case U.S. Pat. No. 5,203,795, the probe element 707 will not intefere with the cutting action of the scissors. In particular, as discussed hereinafter with reference to FIG. 5a, the cutting action will start from the proximal end of the blade 703' and move toward the distal end of the blade 703" without contact ever being made between probe element 707 and the blade 701 of the rotating end effector 790.

Not only is the fixed blade member 792 provided with a rounded terminal probe element 707, but the distal portion 784 of the blade member is also preferably provided with a curvilinear surface 709". Likewise, the transition from the proximal portion 782 to the distal portion 784 of the fixed blade member 792 is preferably curved as indicated at 709". The entire bottom surface of the fixed blade member 792 therefore presents a smooth, curved surface which will not cause trauma to a structure over which it is moved.

Figure 4:
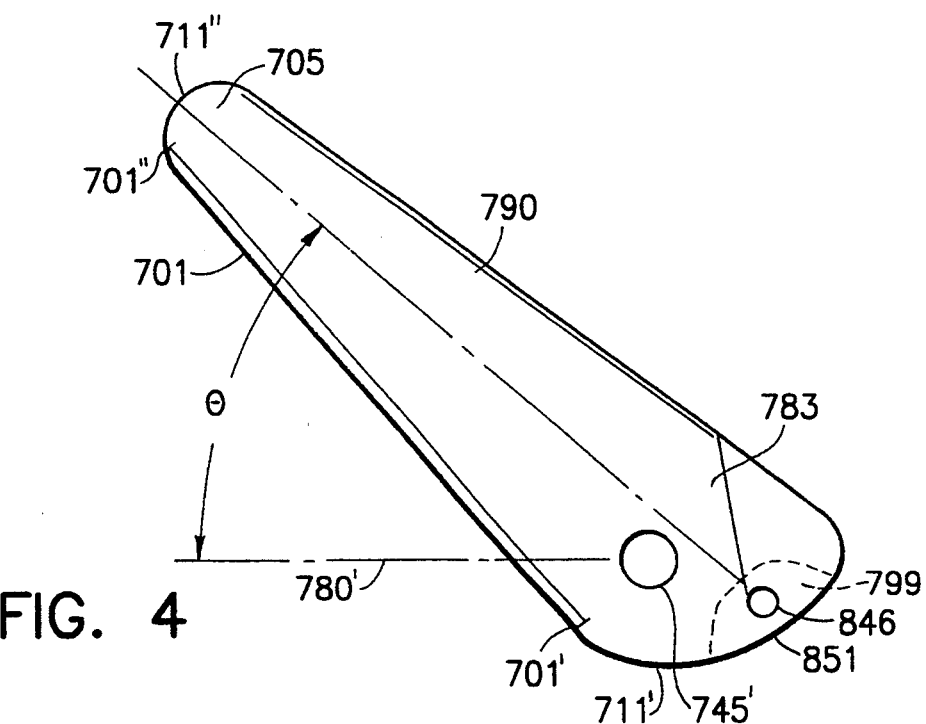
FIGS. 4, 4a and 4b show side elevation, top and bottom views of the rotating blade member of the device of FIG. 1.
Figure 4A:
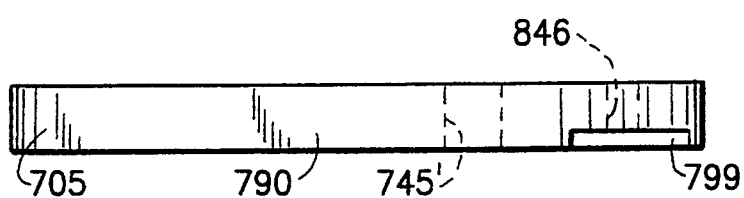
Figure 4B:
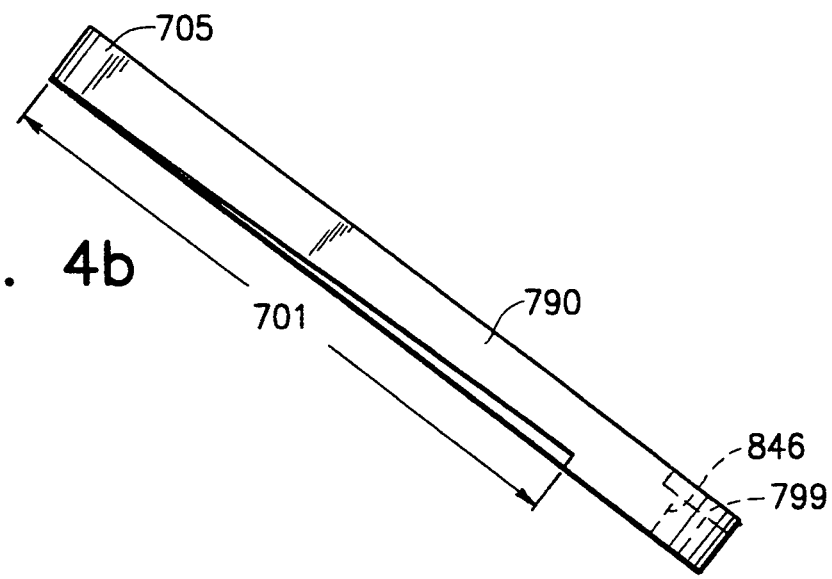

The rotating blade element 790 of the pericardial scissors invention is seen in FIGS. 4, 4a, and 4b. The rotating blade element 790 is provided with a proximal portion 783 which is pivotally mounted at hole 745' to the clevis pin 745, and a distal portion 705 which includes blade edge 701. The proximal portion 783 also includes a second hole 846 through which a means such as the end 797' of a staple 797 (seen in FIG. 5b) or the like extends for coupling the rotating blade element 790 to the push rod of the instrument. In order to accommodate the staple and rotational movement thereof, but maintain desired strength, the proximal portion 783 is provided with a recess or indent 799 in the region surrounding through-hole 846.

As shown in FIG. 4 the central axis 767 of blade member 790 is at an angle Θ with respect to the axis 780' (which is the same axis as the longitudinal axis of the tool or parallel thereto) of its base portion 783 rearward of pivot through-hole 745'. This angle is the same angle at which the distal and proximal portions of the fixed blade member are angled relative to each other.

The distal portion 705 of blade member 790 includes a straight blade edge 701 which extends its entire length (from 701' to 701"). The blade edge is preferably tapered transverse the cutting edge as indicated in FIG. 4b. The distal end of blade member 790 is rounded and presents a completely curvilinear surface 711" in its forward projection as shown in FIG. 4. Preferably, the transition from the proximal portion 783 to the distal portion 705 of the rotating blade member 790 also present a rounded surface 711'. In this manner, blade member 790, as it is slid forward in a closed position relative to and in conjunction with fixed blade member 792 will not present sharp surfaces which could traumatize surrounding tissue structure.

In order to keep possible trauma to surrounding tissue to a minimum, the rotating blade member 790 is designed at its proximal portion 783, such that the distance between the rotation hole 745' and the proximal end surface 798 of the blade member 790 is approximately equal to the vertical distance between hole 745" and the bottom surface 852 of the fixed blade member 792. In this manner, as the rotating blade member 790 rotates relative to the fixed blade member 792 as described hereinafter with reference to FIGS. 5a and 5b, the bottom section of the proximal portion of the rotating blade member 790 will not extend outside the periphery of the fixed blade member 792 and will not traumatize tissue located thereabout.

The fixed and rotating blade members of the pericardial scissors of the invention are seen together in a closed position in FIG. 5a and in an open position in FIG. 5b. The closed position of FIG. 5a is the position in which the scissors are preferably inserted through the trocar tube (axes 880 being an extension thereof). As seen in FIG. 5a, in the closed position, blade 701 of the rotating blade member 790 overlaps blade 703 of the fixed blade member 792, with the rounded ends 711" and 709"/707 of the distal portions 705, 784 effectively adjacent each other and presenting blunt surfaces. Indeed, with the blade members 790 and 792 in closed position, the distal end of blade member 790 is substantially in register with the terminal probe element 707 of blade member 792 so that the most forward projection of the end effector is curved and blunt.

As also seen in FIG. 5a, the end 797' of a staple element 797 is engaging hole 846 in the rotating blade member 790. Blade member 790 and 792 are held in close engagement by clevis 730 and clevis pin 745 which extends through respective holes 745' and 745" of the blade members. Both blade members are held at a sloping angle with respect to the longitudinal axis 780 of the instrument (i.e., the longitudinal axis of the metal tube 15 of FIG. 1). The angle Θ of slope is preferably about 45 degrees, although other angles could be utilized.

Figure 5D:
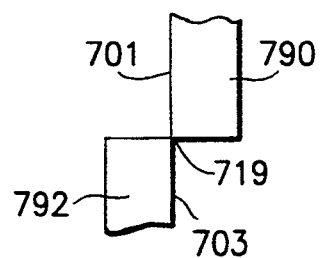
FIG. 5d is a schematic showing the cutting edges of the blade members of FIGS. 3 and 4 forming a cutting location.

Turning to FIG. 5b, it is seen that by use of the push rod 760, blade member 790 is pivotally rotatable from the fully open position of FIG. 5b, where the cutting edge 701 of blade member 790 is substantially perpendicular to the longitudinal axis 780 of metal tube 15, to the closed scissor position of FIG. 5a where the cutting edge 701 is at the sloping angle Θ. As shown in FIG. 5b, the push rod 760 has a flattened distal end 762 having a hole 798. The staple 797 extends through hole 798 and through hole 846 of the rotating blade member 790. With the push rod in a forward position as shown in FIG. 5b, the rotating blade 790 opens relative to the fixed blade 792. As the push rod is pulled backward, rotating blade 790 closes relative to the fixed blade 792. As rotating blade 790 closes, the bearing contact or cutting point 719 (see FIG. 5d) between the blade edges 701 and 703 moves distally from 719 to 719' 719" etc. as indicated in FIG. 5b. It should be noted that protrusion 707, which is slightly set back from edge 703 never contacts blade edge 701 (see FIG. 5c), although the blade edge 703 which is located at the protrusion 707 does make cutting contact with blade edge 701. In this manner, a clean cut can be made without trapping tissue between laterally displaced blade members.

In use, the scissors of the invention is typically used to cut a first membrane or structure (not shown) which is adjacent a second structure (not shown). The tool of the invention is preferably inserted through a trocar tube with the blunt ends of the blade members presenting. Typically, the rotatable blade member 790 is then opened, and the scissors is moved forward such that the fixed blade element 792 is placed between the structure to be cut (between the fixed and rotatable blades), and the structure which is not to be traumatized (under the fixed blade). Activation of the actuation means (e.g., handles) of the scissors effects a cutting action of the first structure, with only the rotatable blade 790 moving. If the first structure is a membrane, after reaching the closed position of FIG. 5a, the actuation means are manipulated to open the rotatable blade 790. The scissors is then slid forward, with flat surface 852 and rounded surface 709' typically contacting but not traumatizing the second structure (e.g., the heart). The cutting is then continued by closing the rotatable blade element 790 as aforedescribed.

If desired, the scissors of the invention can be used in a hook scissors type mode as described in previously incorporated U.S. Pat. No. 5,203,785. In such a case, blade 790 can be opened relative to blade 792 as shown in FIG. 5a, such that a tissue, vein, duct, or other object can be gently moved by the probe element 707 of blade member 792. By partly closing blade 790 relative to blade 792, the object can be pulled away from surrounding tissue by the non-sharpened, non-contacting, blunt edged, probe element 709. With the object 900 so engaged, the object can be pulled to a location away from adjacent tissue where positive identification by imaging or other equipment is achieved. When the identity of the encompassed object is identified, and cutting is desired, the cutting operation along cutting edges 701, 703 proceeds by pivotal movement of blade member 790. With the device of the present invention, a clean cut is provided by cutting edges 701, 703 as blade member 790 and 792 contact each other along a continuously moving bearing contact point 719, 719', 719'' thereby avoiding entrapment of tissue between laterally displaced blade members. Also, since cutting proceeds from one end only, the accidental cutting of an object which can happen using prior art hook scissors is avoided during the procedure of moving the object, as the terminal probe are rounded and blunt.

There has been described and illustrated herein laparoscopic pericardial scissors. While particular embodiments of the invention have been described, it is not intended that the invention be limited exactly thereto, as it is intended that the invention be as broad in scope as the art will allow. Thus, while a scissors having a particular single pivot actuating means utilizing a staple-like element was described, it will be appreciated that different arrangements such as described in U.S. Pat. No. 5,171,258 can be utilized to provide a scissors with additional cutting leverage. Also, while a scissors comprised of particular materials was described, it will be appreciated that other materials could be utilized and that the scissors can have different dimensions. Therefore, it will be apparent to those skilled in the art that other changes and modifications may be made to the invention as described in the specification without departing from the spirit and scope of the invention as so claimed.

What is claimed is:

1. A surgical scissors adapted for insertion through a trocar tube, comprising:
   a) a hollow tube having a proximal and distal ends and a longitudinal axis;
   b) a clevis coupled to said distal end of said hollow tube;
   c) first and second scissor blade means for cutting which are laterally offset from each other and each having proximal and distal portions, said proximal portion of said first scissor blade means having means for pivotally engaging said clevis;
   d) rod means extending at least partially through said hollow tube and having distal and proximal ends, said rod means for coupling to said proximal portion of said first scissor blade means at said distal end of said rod means; and
   e) actuating means engaged to said proximal end of said rod means for imparting reciprocal motion to said rod means relative to said hollow tube which is translated into pivotal motion of said first scissor blade means with said first and second scissor blade means assuming at least a first closed position and a second open position relative to each other, wherein
   said distal portions of said first and second scissor blade means each having an elongate straight blade edge, said elongate straight blade edge of said second scissor blade means extending away from said longitudinal axis at a first angle, and said elongate straight blade edge of said first scissor blade means extending away from said longitudinal axis at a second angle substantially similar to said first angle when said first and second scissor blade means assume said first closed position and at a third angle greater than said first angle when said first and second scissor blade means assume said second open position, said second scissor blade means having a probe element integral with said second blade means at a distal end of said second blade means, said probe element being laterally offset relative to and indented from said elongate straight blade edge of said second blade means and extending away from said second blade means and toward said first blade means, said second blade means with said probe element having a rounded presenting surface, and said first blade means having a rounded distal portion presenting a rounded surface substantially adjacent said rounded presenting surface of said second blade means, and wherein
   rotation of said first scissor blade means from said second open position to said first closed position causes a straight scissors cutting action between said elongate straight blade edges with proximal portions of said blade edges coming together in a bearing contact first, and distal portions of said blade edges coming together in a bearing contact last, wherein said probe portion element does not come in bearing contact with said elongate straight blade edge of said first scissor blade means.

2. A surgical scissors according to claim 1, wherein: said first angle is between about 40 and 50 degrees.

3. A surgical scissors according to claim 2, wherein: said first scissor blade means pivots from said closed position to a fully open position wherein said elongate straight blade edge of said first scissor blade means is substantially perpendicular to said longitudinal axis.

4. A surgical scissors according to claim 1, wherein: said means for pivotally engaging said clevis comprises a first hole in said proximal portion of said first scissor blade means, and
said proximal portion of said first scissor blade means has a second hole, and said surgical scissors further comprises,
a connecting means extending through said second hole and coupling said distal end of said rod means with said first scissor blade means.

5. A surgical scissors according to claim 1, wherein: said proximal portion of said second scissor blade means has a protrusion extending laterally therefrom and engaging said clevis.

6. A surgical scissors according to claim 1, wherein: said proximal portion of said second scissor blade means has a bottom surface, and said proximal portion of said first scissor blade means is shaped such that when said first scissor blade means rotates from said first closed position to said second open position, said first scissor blade means does not extend substantially below a projection of said bottom surface.

7. A surgical scissors according to claim 1, wherein: said proximal portion of said second scissor blade means has a flat bottom surface in a plane substantially parallel to said longitudinal axis, and said proximal portion of said first scissor blade means is shaped such that when said first scissor blade means rotates from said first closed position to said second open position, said first scissor blade means does not substantially extend beyond said plane substantially parallel to said longitudinal axis.

8. A surgical scissors according to claim 7, wherein: said first angle is between about 40 and 50 degrees.

9. A surgical scissors according to claim 8, wherein: said first scissor blade means pivots from said closed position to a fully open position wherein said elongate straight blade edge of said first scissor blade means is substantially perpendicular to said longitudinal axis.

10. A surgical scissors according to claim 9, wherein:

said proximal portion of said second scissor blade means has a protrusion extending laterally therefrom and engaging said clevis, said means for pivotally engaging said clevis comprises a first hole in said proximal portion of said first scissor blade means, said proximal portion of said first scissor blade means has a second hole, and said surgical scissors further comprises, a connecting means extending through said second hole and coupling said distal end of said rod means with said first scissor blade means.

11. In an endoscopic surgical instrument having a hollow tube with proximal and distal ends and a longitudinal axis, a clevis means for coupling to said distal end of said hollow tube, first and second scissor blade means for cutting which are laterally offset from each other and each having proximal and distal portions with the distal portions having elongate straight blade members, said first scissor blade means pivotally engaging said clevis means, and an actuation means extending through said hollow tube and coupled to said first scissor blade means for pivoting said first scissor blade means such that said first scissor blade means assumes at least a first closed position and a second open position relative to said second scissor blade means, an improvement in said first and second scissor blade means comprising:

a) in said first closed position, said first and second scissor blade means extend away from said longitudinal axis at substantially identical first angles, and in said second open position said first scissor blade means extends away from said longitudinal axis at a second angle which is larger than said first angle;

b) said second scissor blade means has a distal portion having an integral probe element which is laterally offset relative to and indented from said elongate straight blade member and extending away from said second scissor blade means and toward said first scissor blade means, said second scissor blade means having a rounded presenting surface, and c) said first scissor blade means has a rounded distal portion presenting a rounded surface substantially adjacent said rounded presenting surface of said second blade member in said first closed position.

12. In the endoscopic surgical instrument of claim 11, wherein:
said second scissor blade means is non-rotationally engaged to said clevis means.

13. In the endoscopic surgical instrument of claim 12, wherein:
said clevis means has a post extending transverse said longitudinal axis, said first scissor blade means has a proximal portion having a first hole pivotally engaging said post which extends therethrough.

14. In the endoscopic surgical instrument of claim 13, wherein:
said second scissor blade means has a proximal portion having a first hole engaging said post of said clevis means and a lateral protrusion engaging said clevis means.

15. In the endoscopic surgical instrument of claim 13, wherein:
said proximal portion of said first scissor blade means has a second hole into which said actuation means couples.

16. In the endoscopic surgical instrument of claim 15, wherein:
said actuation means comprises a push rod having distal and proximal ends and extending through said hollow tube, and connecting means for coupling said distal end of said push rod to said second hole of said first scissor blade means.

17. In the endoscopic surgical instrument of claim 16, wherein:
said distal end of said push rod has a hole therethrough, and
said connecting means comprises a staple element having a first end extending through said hole in said push rod, a second end extending through said second hole in said first scissor blade means, and a middle portion coupling said first and second ends.

18. In the endoscopic surgical instrument of claim 11, wherein:
said first angles are between about 40 and 50 degrees.

19. In the endoscopic surgical instrument of claim 18, wherein:
said second angle is about ninety degrees.

20. In the endoscopic surgical instrument of claim 11, wherein:
said second scissor blade means has a proximal portion with a bottom surface, and said first scissor blade means has a proximal portion shaped such that when said first scissor blade means rotates from said first closed position to said second open position, said first scissor blade means does not extend substantially below a projection of said bottom surface of said second scissor blade means.

* * * * *